(12) United States Patent
Lin et al.

(10) Patent No.: US 11,406,476 B2
(45) Date of Patent: Aug. 9, 2022

(54) MANUAL ORAL CAVITY EXPANSION DEVICE

(71) Applicant: JANMAN PRECISION INDUSTRY CO., LTD., Taoyuan (TW)

(72) Inventors: Chieh-Mao Lin, Taoyuan (TW); Chih-Chung Hu, Taoyuan (TW); Yi-Chian Wang, Taoyuan (TW)

(73) Assignee: JANMAN PRECISION INDUSTRY CO., LTD., Taoyuan (TW)

( * ) Notice: Subject to any disclaimer, the term of this patent is extended or adjusted under 35 U.S.C. 154(b) by 0 days.

(21) Appl. No.: 17/070,665

(22) Filed: Oct. 14, 2020

(65) Prior Publication Data
US 2022/0110716 A1   Apr. 14, 2022

(51) Int. Cl.
| *A61C 7/10* | (2006.01) |
|---|---|
| *A61C 7/02* | (2006.01) |
| *A63B 23/03* | (2006.01) |
| *A61H 1/02* | (2006.01) |
| *A63B 23/00* | (2006.01) |
| *A63B 21/00* | (2006.01) |

(52) U.S. Cl.
CPC ............... *A61C 7/10* (2013.01); *A61C 7/02* (2013.01); *A61H 1/02* (2013.01); *A63B 23/032* (2013.01); *A61H 2205/026* (2013.01); *A63B 21/4047* (2015.10); *A63B 2023/006* (2013.01)

(58) Field of Classification Search
CPC .... A61C 7/10; A61C 7/02; A61C 7/04; A63B 23/032; A63B 21/4047; A63B 2023/006; A63B 23/03; A61H 1/02; A61H 2205/026; A61H 1/00
See application file for complete search history.

(56) References Cited

U.S. PATENT DOCUMENTS

| 1,025,265 | A | * | 5/1912 | Grindle | A61B 17/0206 600/219 |
|---|---|---|---|---|---|
| 3,813,096 | A | * | 5/1974 | Welch | A63B 21/0004 482/11 |
| 4,909,502 | A | * | 3/1990 | Beeuwkes, III | A61H 1/02 482/11 |
| 5,062,191 | A | * | 11/1991 | Carr | B25B 27/205 29/229 |

(Continued)

*Primary Examiner* — Nyca T Nguyen
(74) *Attorney, Agent, or Firm* — Che-Yang Chen; Law Office of Michael Chen

(57) ABSTRACT

An improved manual oral cavity expansion device comprising a fixing element with one end connected with a first holding element, and another end forming an accommodating portion protrudingly disposed with a pivoting portion; at least one linkage element disposed on the fixing element; a rotating element accommodated in an accommodating space of the accommodating portion and sleeved on the pivoting portion; a movable element with one end connected with a second holding element, and another end forming a movable portion correspondingly disposed in the accommodating space and sleeved on the pivoting portion; and an expansion unit. An outer circumference of the rotating element is arranged with a plurality of tooth elements in a row, and one end of the linkage element contacts the tooth elements. The expansion unit has a first expansion arm connected to the accommodating portion and a second expansion arm connected to the movable portion.

10 Claims, 6 Drawing Sheets

(56) References Cited

U.S. PATENT DOCUMENTS

| | | | | |
|---|---|---|---|---|
| 6,708,587 | B1* | 3/2004 | Noniewicz | B25B 5/06 81/313 |
| 7,887,461 | B2* | 2/2011 | Bakhtiyari | A63B 21/025 482/11 |
| 9,867,753 | B2* | 1/2018 | Garay-Arauz | A61H 1/02 |
| 10,086,228 | B2* | 10/2018 | Yoshitake | A61H 1/02 |
| 2003/0080485 | A1* | 5/2003 | Lo | F16B 2/12 269/6 |
| 2005/0211024 | A1* | 9/2005 | Shpakow | G01M 3/3272 81/3.43 |
| 2007/0089752 | A1* | 4/2007 | Christensen, III | A61H 1/0218 128/845 |
| 2007/0287598 | A1* | 12/2007 | Christensen, III | A61H 1/02 482/11 |
| 2008/0264216 | A1* | 10/2008 | Duffy | B25B 7/18 81/302 |
| 2010/0011916 | A1* | 1/2010 | Christensen, III | B25B 9/02 81/342 |
| 2010/0086889 | A1* | 4/2010 | Lindquist | A61C 7/04 433/4 |
| 2018/0085274 | A1* | 3/2018 | Lee | A61B 1/32 |

\* cited by examiner

MANUAL ORAL CAVITY EXPANSION DEVICE

BACKGROUND OF THE INVENTION

Field of Invention

The invention relates to an oral cavity expansion tool, and more particularly to an improved manual oral cavity expansion device that is operated single-handedly to achieve a fixation efficacy.

Related Art

For patients with limited oral cavity opening angle, an oral cavity expansion device is usually required in assisting to perform oral cavity opening exercise, oral cavity cleaning, or medical operations in their oral cavities.

The conventional oral cavity expansion device generally uses the upper and lower rows of incisors and canines in an oral cavity as resistance points. Therefore, in the process of opening an oral cavity, the incisors and the canines will bear a considerable force. If it is not handled properly, the incisors or the canines may be damaged.

In addition, since the conventional oral cavity expansion device must be fixed after the oral cavity is opened to perform medical operations in the oral cavity, a fixing structure is provided on the oral cavity expansion device to ensure that the patient's oral cavity is open. However, since the fixing structure on the conventional oral cavity expansion device must be fixed by manual operation, the patient cannot use only one hand to open the oral cavity, what is more, the patient must be assisted by others, which makes it very inconvenient for the patient to use the conventional oral cavity expansion device.

Therefore, how to solve the above-mentioned problems and drawbacks in the prior art is what the inventor of the invention and relevant manufacturers engaged in this industry are eager to research and make improvement.

SUMMARY OF THE INVENTION

Therefore, in order to effectively solve the above-mentioned problems, a main object of the invention is to provide an improved manual oral cavity expansion device that is operated single-handedly to achieve a fixation efficacy.

A secondary object of the invention is to provide an improved manual oral cavity expansion device that enables a required angle to be adjusted by oneself according to needs.

In order to achieve the above-mentioned objects, the invention provides an improved manual oral cavity expansion device comprising a fixing element, at least one linkage element, a rotating element, a movable element and an expansion unit. One end of the fixing element is connected with a first holding element, and another of the fixing element forms an accommodating portion. The accommodating portion has an accommodating space and is protrudingly disposed with a pivoting portion. The linkage element is correspondingly disposed on the fixing element. The rotating element is correspondingly accommodated in the accommodating space and sleeved on the pivoting portion, an outer circumference of the rotating element is arranged with a plurality of tooth elements in a row, and one end of the linkage element contacts the tooth elements. One end of the movable element is connected with a second holding element, and another end of the movable element forms a movable portion, and the movable portion is correspondingly disposed in the accommodating space and sleeved on the pivoting portion. The expansion unit has a first expansion arm and a second expansion arm, the first expansion arm is connected to the accommodating portion, and the second expansion arm is connected to the movable portion.

In one embodiment, the fixing element further has a first end and a second end, the first end is connected to the first holding element, and the second end forms the accommodating portion, the movable element has a third end and a fourth end, the third end is connected to the second holding element, and the fourth end forms the movable portion.

In one embodiment, the linkage element further has a positioning portion disposed opposite to the fixing element, the positioning portion further extends to form a pressing end and an engaging end, the pressing end is provided for a user to press, and the engaging end meshes with the tooth elements correspondingly.

In one embodiment, the positioning portion further has an upper positioning hole and a lower positioning hole, and an upper positioning pillar and a lower positioning pillar respectively penetrate the upper positioning hole and the lower positioning hole to fix the positioning portion on the fixing element.

In one embodiment, the first expansion arm further has a first connecting end and a first abutting end, the first connecting end is connected with the accommodating portion, the second expansion arm further has a second connecting end and a second abutting end, the second connecting end is connected with the movable portion, and the first and second abutting ends abut with a plurality of molars of a user correspondingly.

In one embodiment, further having an outer cover, the outer cover covers the movable portion correspondingly and is disposed opposite to the accommodating portion, the outer cover has a through hole, and a penetrating element penetrates the through hole and is fixed in the pivoting portion.

In one embodiment, the penetrating element is a countersunk flat head screw.

In one embodiment, the movable portion is further provided with a first hole, the rotating element is further provided with a second hole, and a positioning pin correspondingly penetrates the first and second holes.

In one embodiment, the second holding element further has a plurality of grooves, and the grooves are provided for a user to hold firmly.

In one embodiment, an outer circumference of the rotating element forms an outer peripheral wall, and the tooth elements can be arranged on the outer peripheral wall at equal intervals or unequal intervals.

Through the design of the structure of the invention, after the user holds the first holding element, the expansion unit is inserted into an oral cavity of the user, after correspondingly abutting the first and second abutting ends of the first and second expansion arms against the molars respectively, the second holding element is then pressed to make the second expansion arm gradually move away from the first expansion arm, thereby expanding the oral cavity. At the same time, the movable element drives the movable portion to rotate, thereby driving the rotating element to actuate the linkage element, and the engaging end formed by the linkage element can be correspondingly meshed with the tooth elements, thereby ensuring that the user's oral cavity is open to achieve a fixation efficacy by operating single-handedly by the user, which greatly improves the convenience of use.

DETAILED DESCRIPTION OF THE INVENTION

Figure 1:
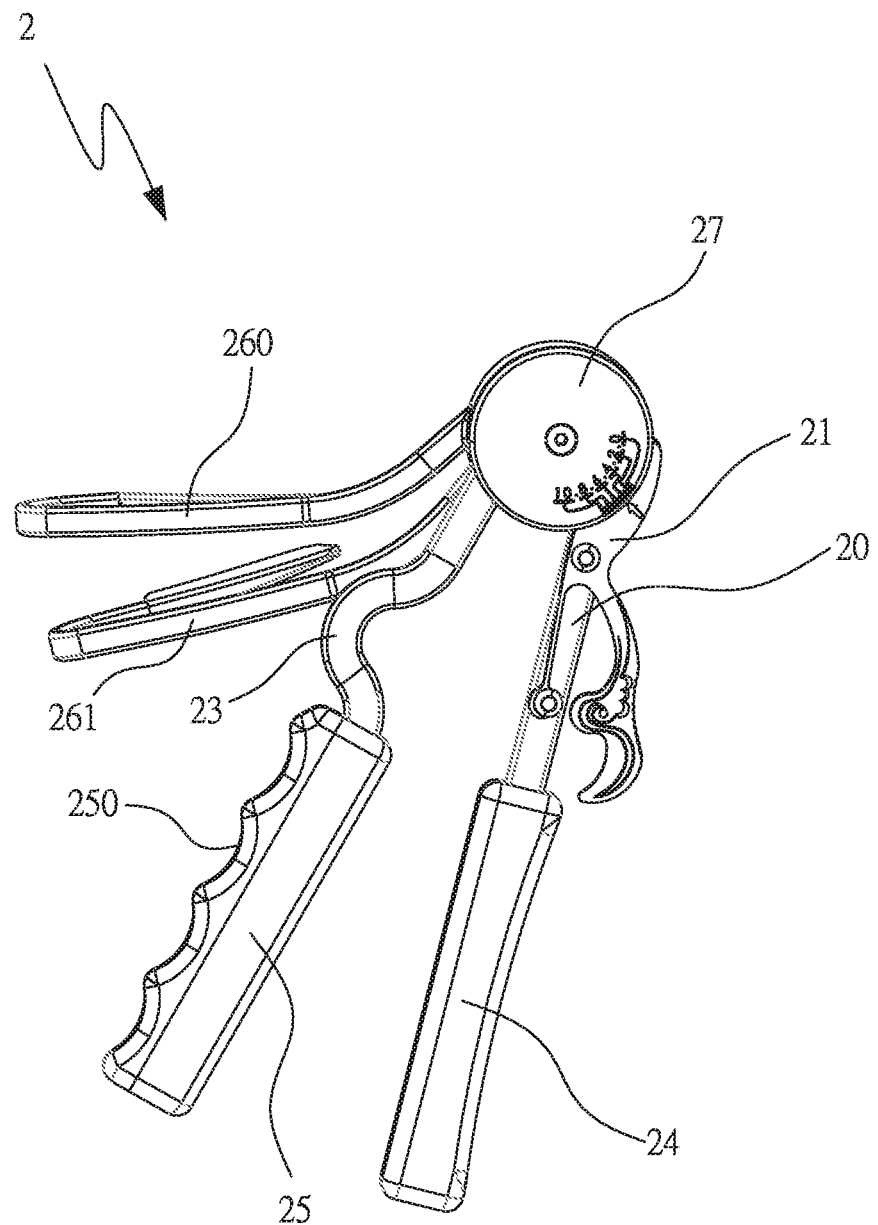
FIG. 1 is a perspective assembly view of an improved manual oral cavity expansion device of the invention.
Figure 2:
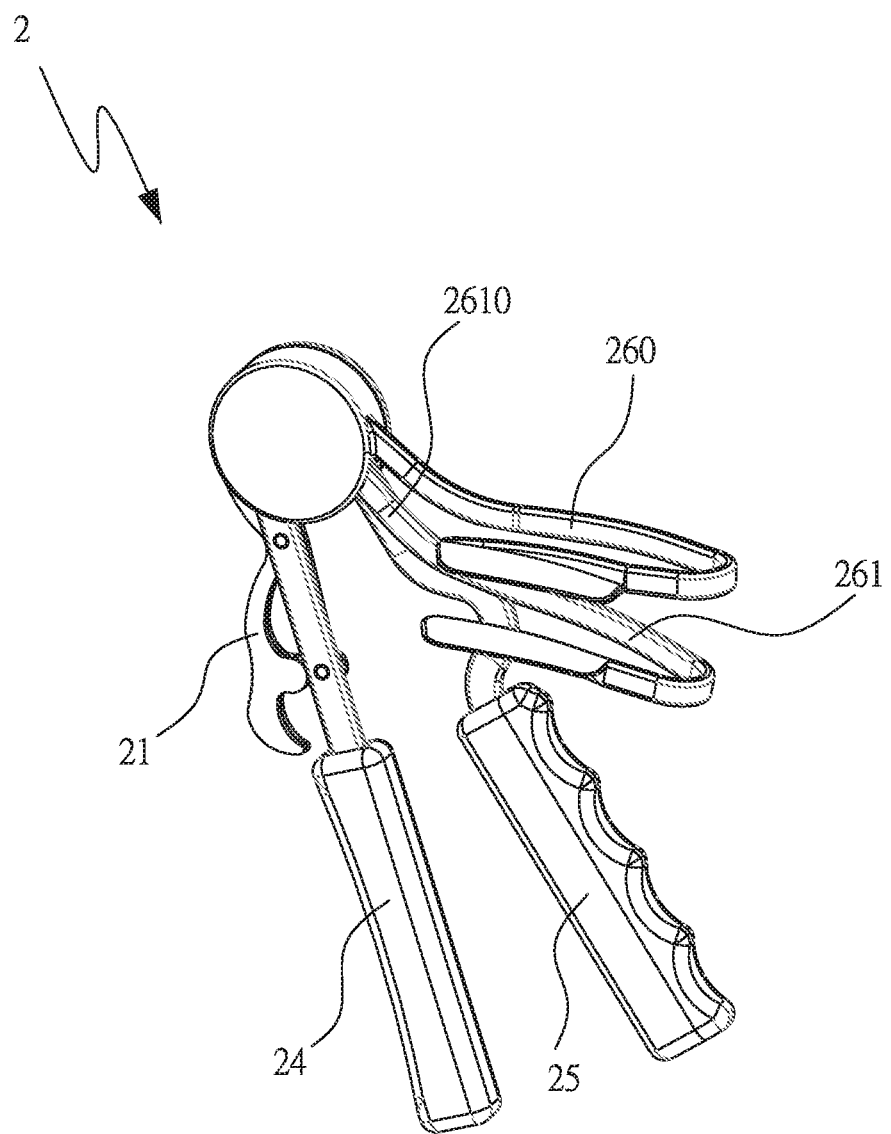
FIG. 2 is a perspective assembly view of the improved manual oral cavity expansion device of the invention viewed from another viewing angle.
Figure 3:
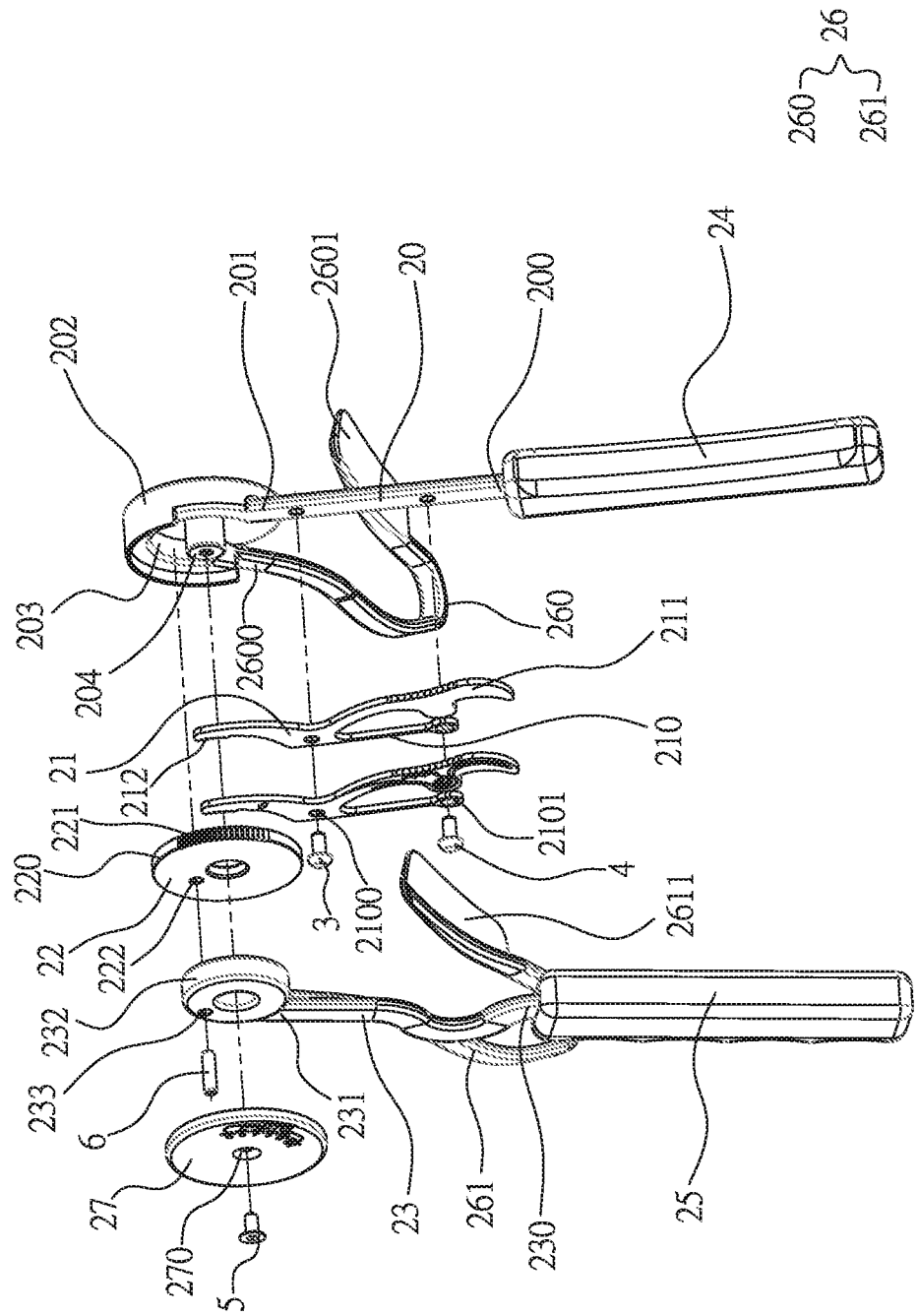
FIG. 3 is a perspective exploded view of the improved manual oral cavity expansion device of the invention.

The above objects of the invention, as well as its structural and functional features, will be described in accordance with the preferred embodiments of the accompanying drawings.

Please refer to FIGS. 1, 2, 3, and 4, which are perspective assembly view, perspective exploded view and partial enlarged view of an improved manual oral cavity expansion device of the invention respectively. As shown in the figures, an improved manual oral cavity expansion device 2 comprises a fixing element 20, at least one linkage element 21, a rotating element 22, a movable element 23, and an expansion unit 26. The fixing element 20 has a first end 200 and a second end 201. The first end 200 is connected with a first holding element 24 for a user 7 to conveniently hold and operate. The second end 201 forms an accommodating portion 202. The accommodating portion 202 has an accommodating space 203, and a pivoting portion 204 is protrudingly formed in the accommodating space 203.

The linkage element 21 has a positioning portion 210 that is disposed opposite to the fixing element 20. The positioning portion 210 further extends to form a pressing end 211 and an engaging end 212. The pressing end 211 is provided for the user 7 to press. The rotating element 22 has a disc-shaped structure and form, and the rotating element 22 is correspondingly accommodated in the accommodating space 203 of the accommodating portion 202 and is rotatably sleeved on the pivoting portion 204. An outer circumference of the rotating element 22 forms an outer peripheral wall 220. The outer peripheral wall 220 is arranged with a plurality of tooth elements 221, and the tooth elements 221 can be arranged on the outer peripheral wall 220 at equal intervals or unequal intervals according to the needs of the user 7. The engaging end 212 contacts the tooth elements 221 correspondingly.

More specifically, the positioning portion 210 further has an upper positioning hole 2100 and a lower positioning hole 2101. An upper positioning pillar 3 and a lower positioning pillar 4 respectively penetrate the upper and lower positioning holes 2100, 2101 to fix the positioning portion 210 on the fixing element 20.

The movable element 23 has a third end 230 and a fourth end 231, the third end 230 is connected to a second holding element 25, the fourth end 231 forms a movable portion 232, and the movable portion 232 is correspondingly disposed in the accommodating space 203 of the accommodating portion 202 and is rotatably sleeved on the pivoting portion 204. It should be explained that the movable portion 232 is further provided with a first hole 233, the rotating element 22 is further provided with a second hole 222, and a positioning pin 6 correspondingly penetrates the first and second holes 233, 222, so that when the movable portion 232 rotates, the rotating element 22 can be driven to rotate at the same time. In addition, the second holding element 25 is further provided with a plurality of grooves 250, and the grooves 250 correspond to the curved shape of the fingers of the user 7 for the user 7 to hold firmly and comfortably.

The expansion unit 26 has a first expansion arm 260 and a second expansion arm 261. The first expansion arm 260 further has a first connecting end 2600 and a first abutting end 2601. The first connecting end 2600 is connected to the accommodating portion 202. The second expansion arm 261 further has a second connecting end 2610 and a second abutting end 2611. The second connecting end 2610 is connected to the movable portion 232. The first and second abutting ends 2601 and 2611 correspondingly abut with a plurality of upper molars 70 and a plurality of lower molars 71 of the user 7 respectively.

In addition, the improved manual oral cavity expansion device 2 further has an outer cover 27, the outer cover 27 covers the movable portion 232 correspondingly and is disposed opposite to the accommodating portion 202. The outer cover 27 further has a through hole 270, and a penetrating element 5 penetrates the through hole 270 of the outer cover 27, the movable portion 232 and the rotating element 22 sequentially and is fixed in the pivoting portion 204. In this embodiment, the penetrating element 5 is a countersunk flat head screw or other equivalents.

Figure 5:
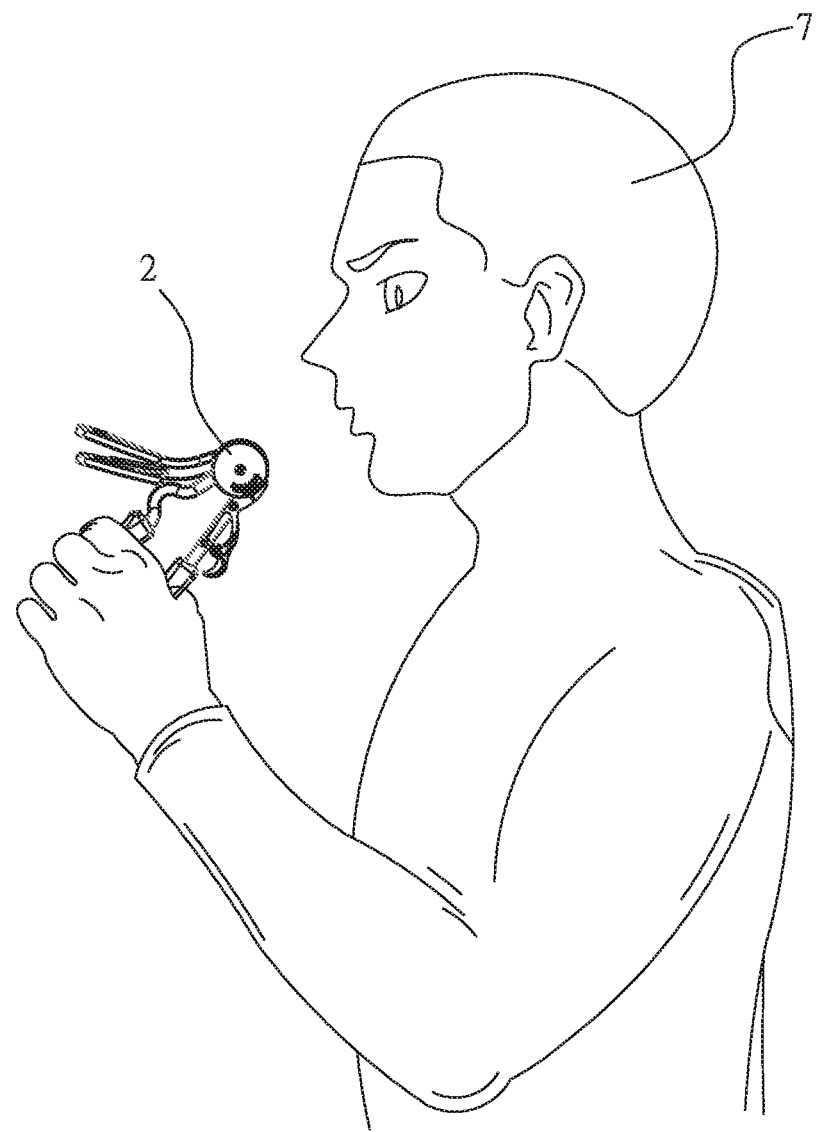
FIG. 5 is a schematic diagram of implementation of the improved manual oral cavity expansion device of the invention.
Figure 6:
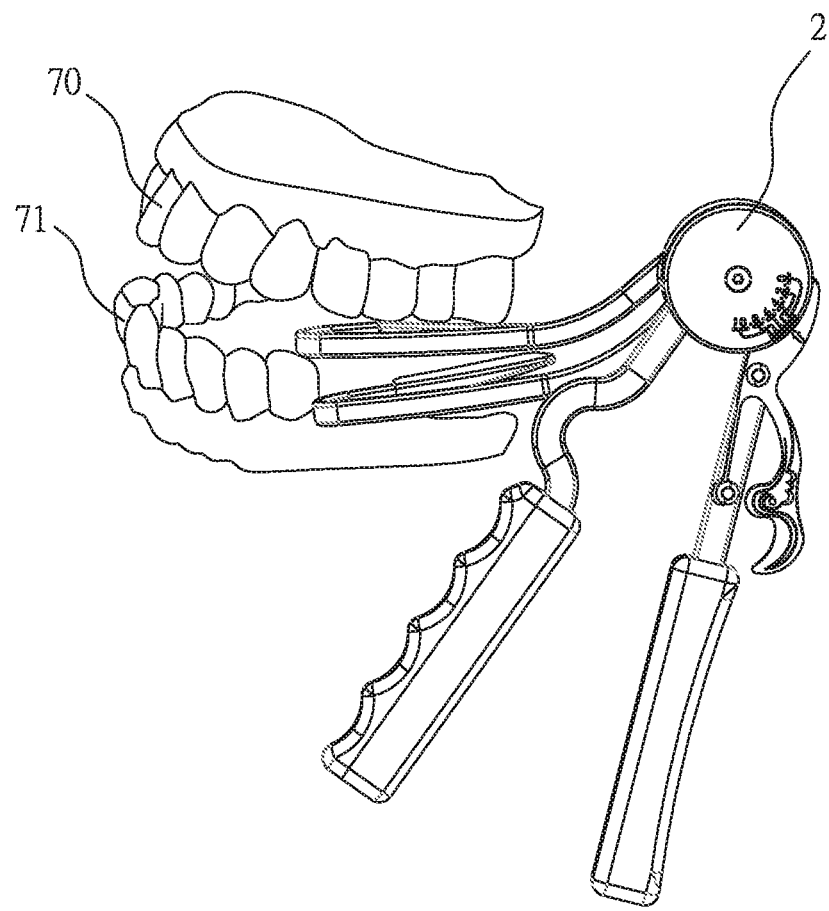
FIG. 6 is a schematic diagram of implementation of the improved manual oral cavity expansion device of the invention.

Please refer to FIGS. 5 and 6 together, which are schematic diagrams of implementation of the improved manual oral cavity expansion device 2 of the invention. Through the design of the structure of the invention, when the user 7 wants to use the improved manual oral cavity expansion device 2, firstly holds the first holding element 24, inserts the expansion unit 26 into the oral cavity, correspondingly abuts the first and second abutting ends 2601 and 2611 of the first and second expansion arms 260, 261 against the upper and lower molars 70, 71 respectively, and then presses the second holding element 25 to make the second expansion arm 261 gradually move away from the first expansion arm 260, thereby expanding the oral cavity. At the same time, the movable element 23 drives the movable portion 232 to rotate, thereby driving the rotating element 22. Since the engaging end 212 of the linkage element 21 contacts the tooth elements 221 of the rotating element 22, the engaging end 212 of the linkage element 21 is also driven to act, so that the engaging end 212 is correspondingly meshed in the tooth elements 221 to form a one-way rotation direction, thereby ensuring that the oral cavity of the user 7 is open and at the same time maintaining positioning to achieve a fixation efficacy by operating single-handedly by the user 7, which greatly improves the convenience of use.

Figure 4:
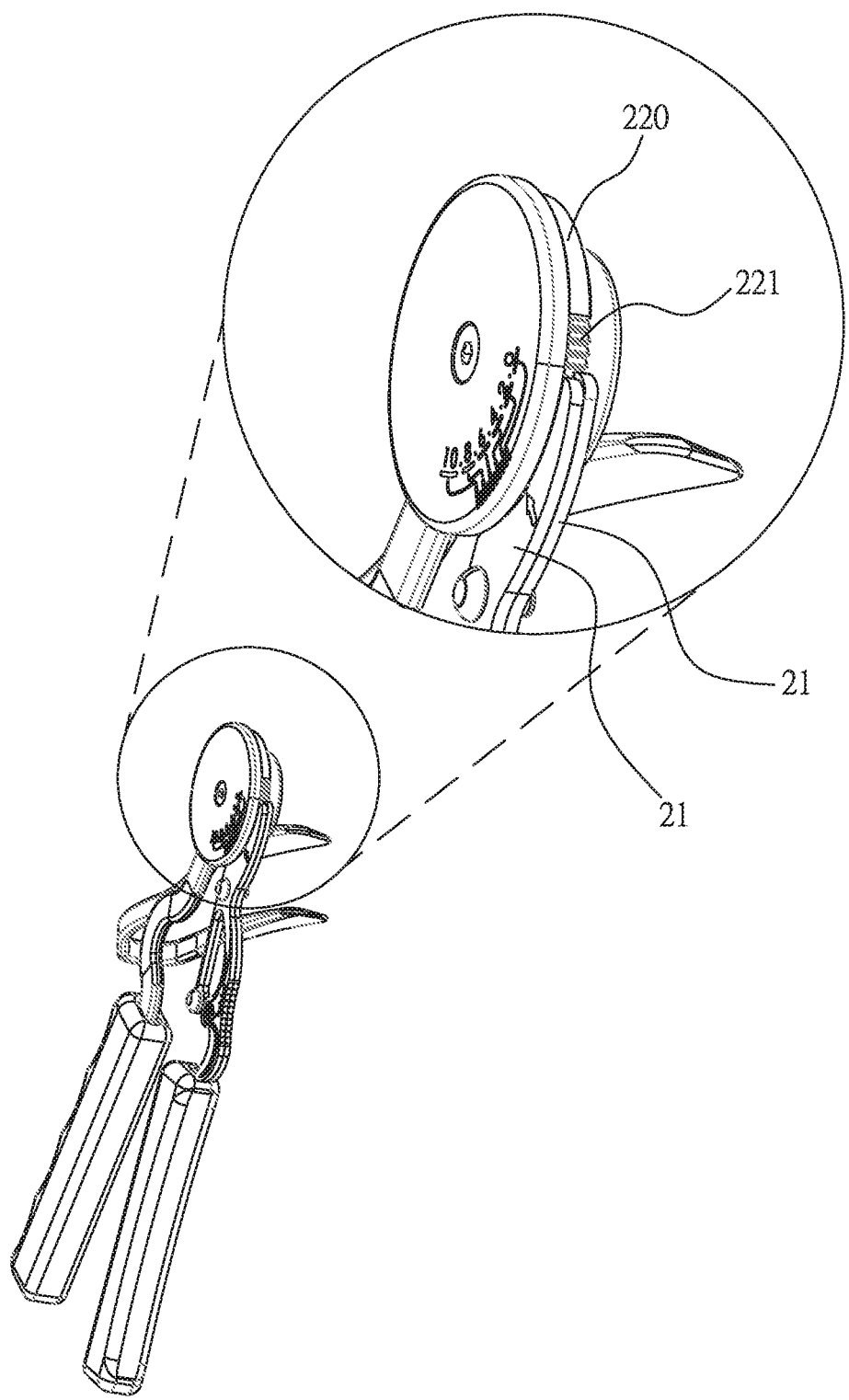
FIG. 4 is a partial enlarged view of the improved manual oral cavity expansion device of the invention.

It should be explained that, in this embodiment, the improved manual oral cavity expansion device 2 is illustrated with two units of the linkage element 21, the two linkage elements 21 are staggered (not overlapping), that is, one of the linkage elements 21 is in contact with a top of one of the tooth elements 221, and the other linkage element 21 contacts at a one-half position between tops of the two tooth elements 221 (as can be seen clearly in FIG. 4). When the rotating element 22 rotates, through the staggered linkage elements 21, the engaging end 212 of each of the linkage elements 21 is meshed in the tooth element 221 in turn, thus increasing a number of segments of the improved manual oral cavity expansion device 2 that can be calibrated. Of course, the user 7 can also use one unit of the linkage element 21 to actuate, but a number of segments is less than that of two units of the linkage element 21. Similarly, three, four or more units of the linkage element 21 can also be used, the more units of the linkage element 21, the more segments can be used.

In summary, compared with the prior art, the invention has the following advantages:

1. One-handed operation is capable of achieving a fixation efficacy;
2. Required angle can be adjusted by oneself according to needs;
3. Significantly improve the convenience of use.

It is to be understood that the above description of the preferred embodiments of the invention is not used to limit the invention, and changes in accordance with the concepts of the invention may be made without departing from the spirit of the invention, for example, the equivalent effects produced by various transformations, variations, modifications and applications made to the configurations or arrangements shall still fall within the scope covered by the appended claims of the invention.

What is claimed is:

1. An improved manual oral cavity expansion device comprising:
    a fixing element, one end thereof being connected with a holding grip as a first holding element, another end thereof forming a depression serving as an accommodating portion, and the accommodating portion having an accommodating space formed by the depression and being protrudingly disposed with a protrusion serving as a pivoting portion;
    at least one linkage element correspondingly disposed on the fixing element;
    a rotating element correspondingly accommodated in the accommodating space and sleeved on the pivoting portion, an outer circumference of the rotating element being arranged with a plurality of tooth elements in a row, and one end of the linkage element contacting the tooth elements;
    a movable element, one end thereof being connected with another holding grip as a second holding element, and another end thereof forming an annular member as a movable portion, and the movable portion being correspondingly disposed in the accommodating space and sleeved on the pivoting portion; and
    an expansion unit having a first expansion arm and a second expansion arm, the first expansion arm being connected to the accommodating portion, and the second expansion arm being connected to the movable portion.

2. The improved manual oral cavity expansion device as claimed in claim 1, wherein the linkage element further has a positioning portion disposed opposite to the fixing element, the positioning portion further extends to form a pressing end and an engaging end, the pressing end is provided for a user to press, and the engaging end meshes with the tooth elements correspondingly.

3. The improved manual oral cavity expansion device as claimed in claim 2, wherein the positioning portion further has an upper positioning hole and a lower positioning hole, and an upper positioning pillar and a lower positioning pillar respectively penetrate the upper positioning hole and the lower positioning hole to fix the positioning portion on the fixing element.

4. The improved manual oral cavity expansion device as claimed in claim 1, wherein further having an outer cover, the outer cover covering the movable portion correspondingly and being disposed opposite to the accommodating portion, the outer cover having a through hole, and a penetrating element having a post penetrating the through hole and being fixed in the pivoting portion.

5. The improved manual oral cavity expansion device as claimed in claim 4, wherein the penetrating element is a countersunk flat head screw.

6. The improved manual oral cavity expansion device as claimed in claim 1, wherein the one end and another end of the fixing element is a first end and a second end, the first end is connected to the first holding element, and the second end forms the accommodating portion, the one end and another end of the movable element is a third end and a fourth end, the third end is connected to the second holding element, and the fourth end forms the movable portion.

7. The improved manual oral cavity expansion device as claimed in claim 1, wherein the first expansion arm further has a first connecting end and a first abutting end, the first connecting end is connected with the accommodating portion, the second expansion arm further has a second connecting end and a second abutting end, the second connecting end is connected with the movable portion, and the first and second abutting ends are configured to abut with a plurality of molars of a user correspondingly.

8. The improved manual oral cavity expansion device as claimed in claim 1, wherein the movable portion is further provided with a first hole, the rotating element is further provided with a second hole, and a positioning pin correspondingly penetrates the first and second holes.

9. The improved manual oral cavity expansion device as claimed in claim 1, wherein the second holding element further has a plurality of grooves, and the grooves are provided for a user to hold firmly.

10. The improved manual oral cavity expansion device as claimed in claim 1, wherein an outer circumference of the rotating element forms an outer peripheral wall, and the tooth elements are arranged on the outer peripheral wall at equal intervals or unequal intervals.

\* \* \* \* \*